(12) United States Patent
Song et al.

(10) Patent No.: US 9,909,981 B2
(45) Date of Patent: Mar. 6, 2018

(54) DIAGNOSTIC DETECTION DEVICE

(71) Applicants: Jun Song, ShenZhen (CN); Liming Pi, ShenZhen (CN); Fengling Chen, ShenZhen (CN); Yuan Yuan, Shenzhen (CN); Yunhai Qiu, ShenZhen (CN)

(72) Inventors: Jun Song, ShenZhen (CN); Liming Pi, ShenZhen (CN); Fengling Chen, ShenZhen (CN); Yuan Yuan, Shenzhen (CN); Yunhai Qiu, ShenZhen (CN)

( * ) Notice: Subject to any disclaimer, the term of this patent is extended or adjusted under 35 U.S.C. 154(b) by 0 days.

(21) Appl. No.: 14/203,493

(22) Filed: Mar. 10, 2014

(65) Prior Publication Data

US 2014/0307260 A1    Oct. 16, 2014

(30) Foreign Application Priority Data

Apr. 16, 2013   (CN) .......................... 2013 1 0129569

(51) Int. Cl.
*G01N 21/47*   (2006.01)

(52) U.S. Cl.
CPC . *G01N 21/4738* (2013.01); *G01N 2021/4752* (2013.01)

(58) Field of Classification Search
CPC ... G01N 2021/4752; G01N 2021/4757; G01N 2021/4776; G01N 21/49; G01N 21/51; G01N 21/513; G01N 21/53; G01N 21/532

USPC .................................................. 356/445, 446
See application file for complete search history.

(56) References Cited

U.S. PATENT DOCUMENTS

| 6,031,661 | A * | 2/2000 | Tanaami ........................ 359/368 |
| 6,246,859 | B1 * | 6/2001 | Takemura ................ B65H 7/04 250/227.11 |
| 7,382,460 | B2 * | 6/2008 | Higashiisogawa G01N 21/4738 356/445 |
| 2002/0191178 | A1 * | 12/2002 | Watkins ............. G01N 21/9501 356/237.2 |
| 2004/0010196 | A1 * | 1/2004 | Wang et al. .................. 600/476 |
| 2006/0087828 | A1 * | 4/2006 | Lin et al. ........................ 362/84 |
| 2011/0242535 | A1 * | 10/2011 | Frose ........................... 356/338 |

\* cited by examiner

*Primary Examiner* — Michael P LaPage
(74) *Attorney, Agent, or Firm* — Weiguo Zhou

(57) ABSTRACT

An optical detection device is provided. The detection device includes a light source emitting light rays, a focusing lens, and a sample testing member. The focusing lens refracts the light rays emitting from the light source to a pre-defined area on the sample testing member and focuses light rays diffusely reflected by the sample testing member. The detection device further includes an aperture diaphragm having an aperture. The aperture is configured to allow the focused reflected light rays to pass through. The detection device further includes a photodetector configured to receive the focused reflected rays passing through the aperture.

5 Claims, 3 Drawing Sheets

DIAGNOSTIC DETECTION DEVICE

CROSS-REFERENCES TO RELATED APPLICATIONS

This application claims priority of Chinese Patent Application 201310129569.3, filed on Apr. 16, 2013, the entire contents of which are hereby incorporated by reference.

FIELD OF INVENTION

This invention relates generally to a medical device and, more particularly, to a medical device to detect chemicals.

BACKGROUND

With the improvement of living standards, a person is becoming more attentive to his or her own health status indicators. It has become necessary or desirable to monitor certain metabolites produced in the body. Routine, regular and frequent test of certain metabolites, such as blood sugar and blood lipids, or chemical indicators of the body, such as pH value of the blood, may encourage people to take certain health measures. Traditional tests conducted in hospital are usually time-consuming and costly and not suitable for regular and frequent tests.

Portable biochemical detectors were created to meet the need for regular test. Certain portal detection devices detect the concentration or amount of metabolites in the body using photoelectric colorimetry. A photoelectric colorimetry based device usually includes a light source with multiple lights. The light rays emitting from the source may pass through an optical plate, which may be transparent, and illuminate on a test paper. The diffusely reflected light then passes through the optical plate. An aperture diaphragm stops the passage of diffusely reflected light, except for the light passing through the aperture to reach a photoelectric detector. Thus, the light received by the detector is only a small portion of the reflected light and weak. Meanwhile, light from other source, such as the light reflected from the optical plate, may reach the detector to create noise. As a result, the signal to noise ratio may be small. It may become necessary to collect large amount of sample, such as blood, from a patient to conduct a test, which may increase the pain a patient might suffer.

The disclosed medical device is directed at solving one or more problems set forth above and other problems.

BRIEF SUMMARY OF THE DISCLOSURE

One aspect of the present disclosure provides an optical detection device. The detection device includes a light source emitting light rays, a focusing lens, and a sample testing member. The focusing lens focuses the light rays emitting from the light source to a pre-defined area on the sample testing member and focuses light rays diffusely reflected by the sample testing member. The detection device further includes an aperture diaphragm having an aperture. The aperture is configured to allow the focused reflected light rays to pass through. The detection device further includes a photodetector configured to receive the focused reflected rays passing through the aperture.

Other aspects of the present disclosure can be understood by those skilled in the art in light of the description, the claims, and the drawings of the present disclosure.

DETAILED DESCRIPTION

Reference will now be made in detail to exemplary embodiments of the invention, which are illustrated in the accompanying drawings. Wherever possible, the same reference numbers will be used throughout the drawings to refer to the same or like parts.

Figure 1:
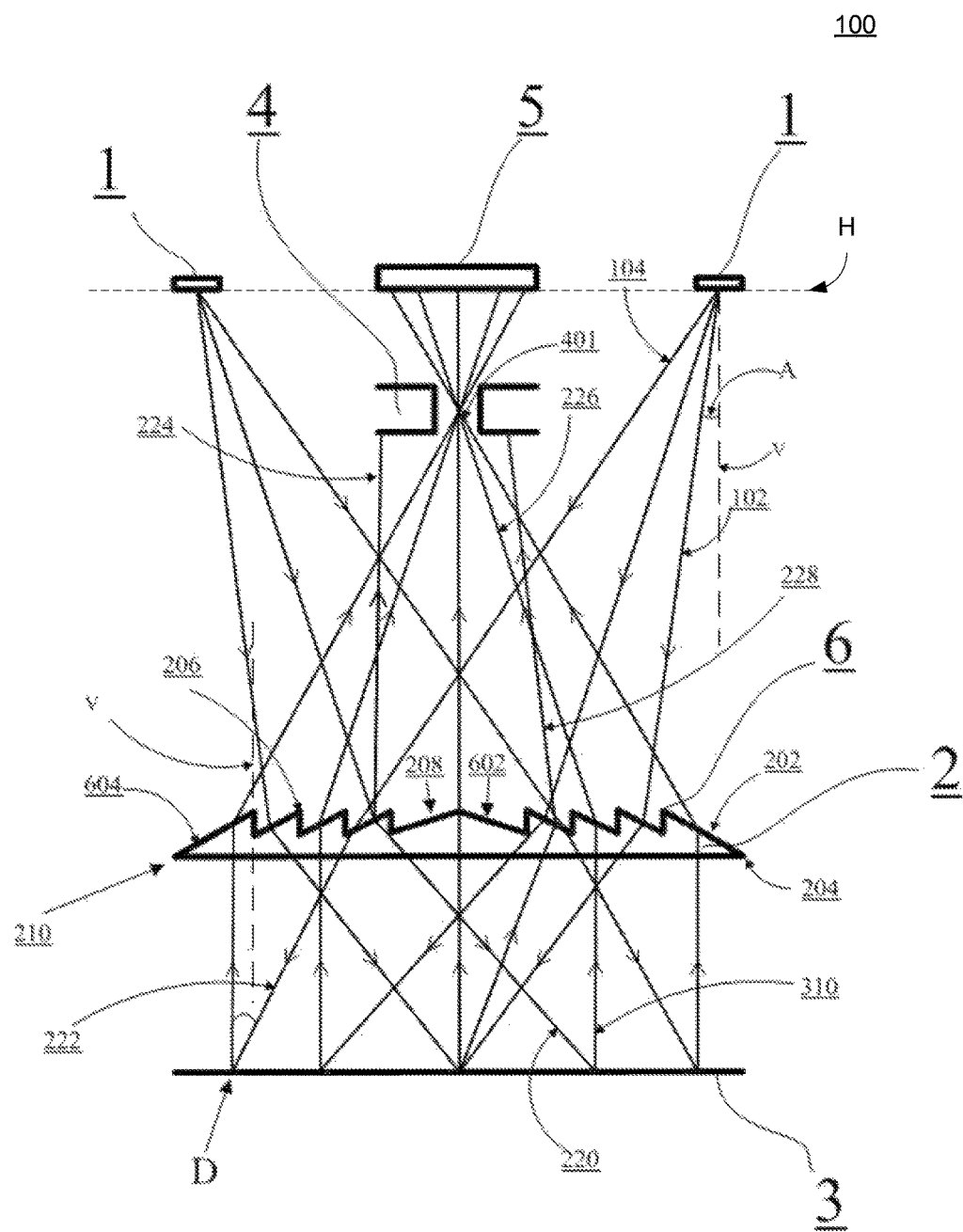
FIG. 1 illustrates an exemplary detection device consistent with the disclosed embodiments.

FIG. 1 illustrates an exemplary detection device 100 consistent with the disclosed embodiments. As shown in FIG. 1, the detection device 100 includes a light source 1, a lens 2, a sample testing member 3, an aperture diaphragm 4, and a photodetector 5.

The light source 1 emits a light ray 102. In certain embodiments, the light source 1 is a multi-lights light source. That is, the light source 1 may include a plurality of lights. The light source 1 may also be a single light. The plurality of lights of the light source 1 may or may not be located on a same surface. In certain embodiments, the plurality of lights of the light source 1 may be located on a first surface H.

The wavelength of the light emitting from the light source may be adjusted. The optimal wavelength for detecting certain chemical may be determined by the material absorption bands. In certain embodiments, the light source 1 may be one or a plurality of surface mount light-emitting diode (SMD LED).

The lens 2 may be a focusing lens. The lens 2 may be in any appropriate shape. For example, the lens 2 may be a spherical lens, an aspherical lens, or a cylindrical lens. Other appropriate shapes may also be used. In certain embodiments, the lens 2 may be a Fresnel lens. Other types of lens, such as convex lens, may also be used. The Fresnel lens 2 may be in a substantially circular shape. The Fresnel lens 2 may also be in other appropriate shapes. As shown in FIG. 1, the Fresnel lens 2 has two sides, a first side 202 facing the light source, and a second side 204 facing the sample testing member.

Figure 2:
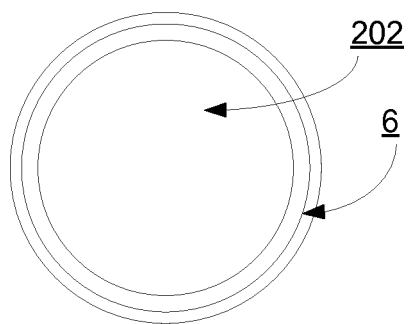
FIG. 2 illustrates a cross section view of a top side of an exemplary Fresnel lens consistent with the disclosed embodiments.

FIG. 2 illustrates a cross section view of the first side 202 of the exemplary Fresnel lens 2, consistent with the disclosed embodiments. As shown in FIGS. 1 and 2, the first side 202 of the Fresnel lens 2 may be divided into a set of concentric annular sections 6.

Returning to FIG. 1, FIG. 1 illustrates a side cross section view of the Fresnel lens 2 used in the detection device 100 consistent with the disclosed embodiments. Each annular section 6 except the annular section 6 in the center includes a first plane 206 and a second plane 208. The first plan 206 faces the center of the circle. The first plane 206 may be substantially parallel to a second surface V or forms a small angle with the surface V. The second plane 208 may be a bevelled plane declining from the top of the plane 206 to the bottom of the next plane 206 located further from the center. For the annular section 602 at the center of the Fresnel lens 2, the surfaces 206 of the two adjacent sections 602 merge. For the annular section 604 at the edge of the Fresnel lens 2, the bevelled plane 208 declining to the edge 210 of the Fresnel lens 2. The bevelled plane of the second plane 208 may be substantially planar or curved. The second side 204 of the Fresnel lens 2 may be a substantially flat surface and substantially smooth.

The sample testing member 3 may be configured to contain a sample to be tested. A chemical reaction between a sample and a reagent may occur on the sample testing member 3. For example, a blood sample may be placed on the sample testing member 3 and may react with certain enzyme or chemical to generate one or more products that may reflect light to be detected by the photodetector 5. In certain embodiments, the sample testing member 3 is a test strip. Other type of testing member may also be used.

Figure 3A:
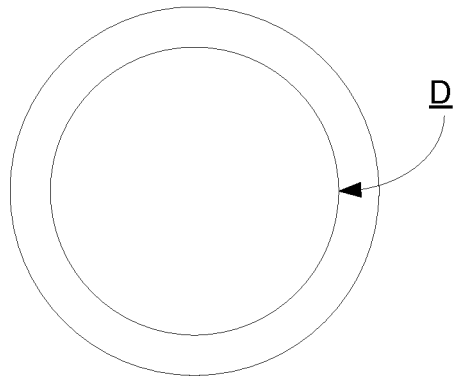
FIGS. 3A and 3B illustrate a cross section view of an exemplary testing member consistent with the disclosed embodiments.
Figure 3B:
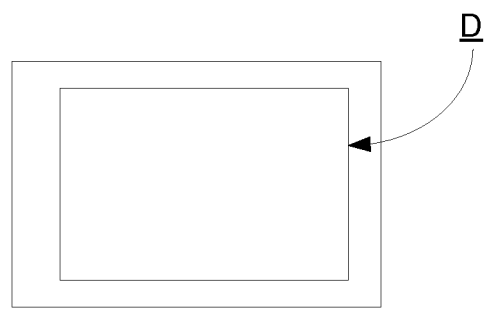

FIGS. 3A and 3B illustrates a cross section view of an exemplary testing member 3 consistent with the disclosed embodiment. As shown in FIGS. 3A and 3B, a border D is located within the testing member 3. The border D may be slightly protruded from the testing member 3 to allow the sample to be confined within the border D. Other appropriate mechanisms may be used to contain the samples within the border D of the testing member 3. The border D may be in the similar shape as the testing member 3. The border D may or may not be in a same shape as the sample member 3. FIG. 3A illustrates the testing member 3 in a circular shape. FIG. 3B illustrates the testing member 3 in a rectangular shape. The testing member 3 may be in other appropriate shapes.

As shown in FIG. 1, the light source 1 emits a light ray 102 that form an angle A with the surface V. In certain embodiments, the angle A is between 10° to 45°. The light source 1 may be configured to limit the range of the light ray 102. For example, the light source 1 may be configured so that the light ray 102 may not reach the photodetector 5 directly.

The light ray 102 may be refracted to a light ray 220 after it passes through the lens 2. The lens 2 may be configured so that the light ray 220 may be restricted within certain area on the sample testing member 3. For example, as shown in FIG. 1, when the angle A reaches the maximum, the light ray 104 may be refracted to a light ray 222. The light ray 222 may be restricted within the border D on the sample testing member 3.

The lens 2 may also reflect the light ray 102 to a reflected light ray 224. As shown in FIG. 1, the reflected light ray 224 may be blocked by the aperture diaphragm 4 so the light ray 224 may not reach the photodetector 5.

The testing member 3 reflects the light ray 220 to light ray 310. The intensity of the light ray 310 reflected from the sample testing member 3 generally follows the Lambert's Law of Reflection. The intensity of a particular light ray may be expressed as $I_\lambda(\theta) = I_{\lambda,0} \cos \theta$, where $I_\lambda$ is the intensity of reflected light ray, $I_{\lambda,0}$ is the intensity of the reflected light ray in the surface normal, θ is the angle between reflected ray and the surface normal. For a particular reflecting element, the intensity of the reflected light ray 310 reaches the maximum on the surface normal.

The light ray 310 may be refracted by the lens 2 to become a refracted light ray 226. The aperture diaphragm 4 is configured to allow certain portion of the light 226 passing through an aperture 401. In certain embodiments, the aperture 401 is located at the focal point of the lens 2 and allows the focused reflected light 226 to pass. The aperture diaphragm 4 may block the light from other sources and certain portion of the reflected lights. For example, the aperture diaphragm 4 may block the light 224 reflected by the lens 2. The aperture diaphragm 4 may also block light from ambient sources and a diffusely reflected light ray 222 that is not focused.

The photodetector 5 may receive the light 226 passing through the aperture 401. The photodetector 5 may be an appropriate detector that may transform the light signal into electrical signal or digital signal. In certain embodiment, the photodetector 5 is a photodiode. Other appropriate types of photodetectors may also be used. The photodetector 5 may be in any appropriate size or shape. In certain embodiment, the photodetector 5 may be in a shape of circular disc or square disc. The photodetector 5 may be in other shape.

The photodetector 5 may transform the light signal received into an electrical signal or a digital signal. The transformed electrical signal or digital signal may be representative of the intensity or strength of the light signal received. For example, the transformed electrical or digital signal may be linearly proportional to the light signal received by the photodetector 5. The transformed electrical or digital signal may also have other type of mathematical relationship to the light received. The electrical signal or the digital signal may be then transferred to a second device to process, analyze, display and/or record the intensity of the reflected light. The second device may be a microcontroller unit with software for the signal analysis. The second device may also perform other tasks with respect to the signals received. The light signal received by the photodetector 5 may also be transformed to other type of signal that may be received, analyzed, and displayed. The second device may also be integrated with the photodetector 5.

In certain embodiments, a photocurrent signal which indicates the level of the intensity of the light may be obtained using an optical-electrical transforming component, such as a silicon-photodiode. The photocurrent may be transformed into a voltage signal through a current voltage conversion circuit. By analog-to-digital conversion, the analog voltage may be transformed into digital voltage signals. The digital signals may be analyzed and displayed. The process may be performed using a commercially available electrical signal reader such as Roche's glucose meter.

The relative location of the light source 1, the lens 2, and the sample testing member 3 may be configured to allow refracted light ray 226 to be focused in a pre-defined area. That is, a significant portion of refracted light ray 226 is focused within a pre-defined area. The configuration of the light source 1, the lens 2, and the sample testing member 3 may also allow the light ray 226 to having sufficient intensity when it reaches the sample testing member 3. Further, the configuration may allow the easy handling of the sample testing member 3. In certain embodiments, the distance between the light source 1 and the lens 2 is about 3 millimeter (mm). In certain embodiments, the distance between the lens 2 and the sample testing member 3 is about 1 millimeter (mm). The distances between the light source 1 and the lens 2 and between the lens 2 and the sample testing member 3 may be adjusted empirically.

The light ray 220 may be reflected by the sample testing member 3 to become a reflected light ray 310. The light ray 310 may be refracted again by the lens 2 and become light ray 226. The lens 2 is configured to refract a significant portion of the light rays 310 so that a significant portion of the focused light rays 226 may pass through the aperture 401. For the light ray that is not focused to the aperture 401, such as the light ray 228 as shown in FIG. 1, the aperture diaphragm is configured to block the light rays 228 so they may not reach the photo detector 5.

The photodetector 5 may be configured to receive the light rays 226 passing through the aperture 401. In certain embodiments, the photodetector 5 is located directly above the aperture 401. The photodetector 5 may or may not be located at the same surface as the light source 1 is located. In certain embodiments, the photodetector 5 may be located on the surface H where the light source 1 is located. The photodetector 5 may be located at other locations and such locations may be determined empirically.

Example 1

Experiments were designed to demonstrate the effect of the presently disclosed detection device. An exemplary detection device consistent with the disclosed embodiments was used. In the exemplary detection device, the photodetector 5 is located about 3 mm from the lens 2. The lens 2 is a Fresnel lens. Two detectors 5 were used, the first one being about 6 mm by 6 mm in size and the second one being about 0.5 mm by 0.5 mm in size. An optical stimulation software ZEMAX simulated optical system was used to analyze the collected signals from the detector 5. A device with a Fresnel lens consistent with disclosed embodiment was compared with a device with a planar plate in the place of the lens 2.

When the detector with 6 mm by 6 mm in size was used, the signal received by detector 5 was increased by 32% in the device with Fresnel lens consistent with the disclosed embodiment compared to the device using a planar plate. When the detector with 0.5 mm by 0.5 mm in size was used, the signal received by detector 5 was increase by 34% in the device with Fresnel lens consistent with the disclosed embodiment compared to the device using a traditional planar plate.

Example 2

Experiments were designed to investigate the level of noise the photodetector 5 received. A photocurrent signal which indicates the level of the light intensity may be obtained using an optical-electrical transforming circuit. The photocurrent may be transformed into a voltage signal through a current voltage conversion circuit. By analog-to-digital conversion, the analog voltage may be transformed into digital voltage signals. The digital signals may be recorded, analyze and displayed.

When there was no lens in a detection device, which includes the light source 1, the sample testing member 3, the aperture diaphragm 4, and the photodetector 5, but not the lens 2, a background value of 54 was obtained. When an exemplary device 100 consistent with the disclosed embodiments with a Fresnel lens 2 was used, a noise value of 241 was obtained. When a device that is similar to a detection device 100 consistent with the disclosed embodiment except that an acrylic plate was in the place of the focusing lens 2 was used, a noise value of 1012 was obtained. Thus, the noise value generated by the Fresnel lens was 187 (241−54), and the level of noise generated by the acrylic plate was 958 (1012−54).

Example 3

Experiments are designed to investigate the signal collecting efficiency and the signal noise ratio of an exemplary device 100 consistent with the disclosed embodiments. Five samples of $H_2O_2$ solution with different concentration were prepared. Fifteen micro-liters (15 μl) of each sample were loaded on sample testing member 3, in this case, a test strip. The same process as described in Example 2 was used to generate the digital signal for recording, analyzing and displaying. The result is shown in Table 1 and Table 2.

TABLE 1

The effect of Fresnel lens on signal strength

| concentration of $H_2O_2$ | Signal intensity | | Increase rate of signal intensity |
|---|---|---|---|
| | Detection device with planar plate lens | Detection device with Fresnel lens | |
| 4.569 | 528 | 651 | 23.30% |
| 5.548 | 424 | 547 | 29.01% |
| 6.527 | 341 | 432 | 26.69% |
| 7.507 | 308 | 389 | 26.30% |
| 8.486 | 278 | 356 | 28.06% |
| Average | | | 26.67% |

TABLE 2

The effect of Fresnel lens on signal to noise ratio (SNR)

| concentration of $H_2O_2$ | Detection device with planar plate lens | | | Detection device with Fresnel lens | | | Increase of SNR (dB) using Fresnnel lens |
|---|---|---|---|---|---|---|---|
| | Effective Signal | Noise | SNR | Effective Signal | Noise | SNR | |
| 4.569 | 528 | 1165 | −6.87384 | 651 | 292 | 6.963963 | 13.84 |
| 5.548 | 424 | 1165 | −8.7792 | 547 | 290 | 5.511787 | 14.29 |
| 6.527 | 341 | 1161 | −10.6416 | 432 | 291 | 3.431815 | 14.07 |
| 7.507 | 308 | 1156 | −11.4881 | 389 | 293 | 2.46164 | 13.95 |
| 8.486 | 278 | 1154 | −12.3632 | 356 | 295 | 1.63256 | 14.00 |
| Average | | | | | | | 14.03 |

As shown in Table 1, the use of a Fresnel lens may increase the intensity of the signal received by the photodetector. As shown in Table 2, the use of Fresnel lens may increase the signal to noise ratio. The value of SNR is determined by the formula below.

$$SNR = 20 \times \log\left(\frac{\text{signal}}{\text{noise}}\right)$$

The detection device according to the present disclosure may increase the signal and reduce signal noise. As a result, a person using the detection device according the present disclosure only need a smaller amount of sample for test. In some instance, for example, when the sample to be tested is blood, using a detection device according to the present disclosure may reduce the pain a person suffers.

While various embodiments in accordance with the present invention have been shown and described, it is understood that the invention is not limited thereto. The present invention may be changed, modified and further applied by those skilled in the art. Therefore, this invention is not limited to the detail shown and described previously, but also includes all such changes and modifications. For example, a device according to the present disclosure may be adjusted to detect metabolites or other chemicals in blood, urine or other body fluid. A device according to the present disclosure may also be used for testing conducted for animals.

What is claimed is:

1. An optical detection device, comprising:
a light source emitting light rays, wherein the light source comprises a first light source and a second light source;
a Fresnel lens, wherein the light rays reach the Fresnel lens directly;
a sample testing member, wherein the Fresnel lens focuses the emitted light rays emitting from the light source to a pre-defined area on the sample testing member and focuses light rays diffusely reflected by the sample testing member;
an aperture diaphragm located directly above the Fresnel lens, the aperture diaphragm having an aperture, wherein the reflected light rays on a plane normal to the sample testing member are refracted by the Fresnel lens to pass through the aperture, further wherein the aperture selectively allows the reflected light rays on the plane normal to the sample testing member to pass after being refracted by the Fresnel lens; and
a photodetector configured to receive directly the reflected rays focused by the Fresnel lens and passing through the aperture, wherein the photodetector is located directly above the aperture, wherein:
the photodetector is located at a first surface where the first light source and the second light source are also located, and where the first light source and second light source are symmetrically arranged on either side of the photodetector;
the aperture diaphragm is located between the photodetector and the Fresnel lens and is so configured that the emitted light rays from the light source do not pass through the aperture.

2. The detection device according to claim 1, wherein:
the aperture is configured to be located at the focal point of the Fresnel lens.

3. The detection device according to claim 1, wherein:
the first light source and the second light source are SMD LED light sources.

4. The detection device according to claim 1, wherein:
the light rays emitting from the light source forms an angle with a plane normal to the first surface, and the angle is between about 10° to 45°.

5. The detection device according to claim 1, wherein:
the Fresnel lens is substantially circular, and
the Fresnel lens has a first side and a second side, the second side being flat and smooth, the first side being divided into a plurality of concentric annular sections, wherein:
each annular sections has a center facing plane and a bevelled plane, the bevelled surface declining from the top of the center facing plane to the bottom of the center facing plane of the next annular section which is further from the center.

* * * * *